US006559274B2

(12) United States Patent
Gertzmann et al.

(10) Patent No.: US 6,559,274 B2
(45) Date of Patent: May 6, 2003

(54) STABILIZED MONOASPARTIC ACID ESTERS AND POLYASPARTIC ACID ESTERS

(75) Inventors: Rolf Gertzmann, Leverkusen (DE); Lutz Schmalstieg, Köln (DE); Stefan Groth, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/974,939

(22) Filed: Oct. 10, 2001

(65) Prior Publication Data

US 2002/0132965 A1 Sep. 19, 2002

(30) Foreign Application Priority Data

Oct. 11, 2000 (DE) .......................................... 100 50 137

(51) Int. Cl.$^7$ ............................................... C08G 69/10
(52) U.S. Cl. ...................... 528/328; 528/332; 528/337; 528/44; 528/52; 528/75; 528/83
(58) Field of Search ............................ 528/328, 332, 528/337, 44, 52, 75, 83

(56) References Cited

U.S. PATENT DOCUMENTS

| 5,126,170 A | 6/1992 | Zwiener et al. .......... 427/385.5 |
| 5,214,086 A | 5/1993 | Mormile et al. ............. 524/237 |
| 5,216,170 A | 6/1993 | Lindel et al. ................ 546/300 |
| 5,236,741 A | 8/1993 | Zwiener et al. .......... 427/385.5 |
| 5,243,012 A | 9/1993 | Wicks et al. .................. 528/58 |
| 5,364,955 A | 11/1994 | Zwiener et al. ............. 556/418 |
| 5,412,056 A | 5/1995 | Zwiener et al. ............... 528/73 |
| 5,489,704 A | 2/1996 | Squiller et al. ............... 560/35 |
| 5,623,045 A | 4/1997 | Zwiener et al. ............... 528/68 |
| 5,821,326 A | 10/1998 | Kurek et al. ................ 528/332 |

FOREIGN PATENT DOCUMENTS

| DE | 197 01 835 | 7/1998 |
| EP | 0 667 362 | 8/1995 |
| EP | 0 893 458 | 1/1999 |

*Primary Examiner*—Duc Truong
(74) *Attorney, Agent, or Firm*—Joseph C. Gil; Thomas W. Roy

(57) ABSTRACT

The present invention relates to a composition comprising monoaspartic acid esters and polyaspartic acid esters as well as an addition product prepared from an unsaturated dicarboxilic acid compound and a thiol, a process for their production, and their use as reactive component for polyisocyanates in two-component polyurethane systems.

12 Claims, No Drawings

STABILIZED MONOASPARTIC ACID ESTERS AND POLYASPARTIC ACID ESTERS

BACKGROUND OF THE INVENTION

The present invention relates to compositions based on monoaspartic acid esters and polyaspartic acid esters, a process for their production, and their use as reactive components for polyisocyanates in two-component polyurethane systems.

Two-component (2K) coating agents that contain as binder a polyisocyanate component in combination with a component reactive with respect to isocyanate groups, in particular a polyhydroxyl component, have been known for a long time. They are suitable for the production of high-quality coatings that are hard, elastic and resistant to abrasion and solvents, and that in particular can also be formulated to resist weathering.

In the field of 2K-polyurethane coating technology, specific ester group-containing secondary polyamines have recently become established that are in particular suitable, in combination with lacquer polyisocyanates, as binders in low-solvent or solvent-free high-solid coating compositions and that permit a rapid hardening of the coatings at low temperatures.

These secondary polyamines are the so-called polyaspartic acid esters such as are described for example in EP-A 0 403 921. Their use alone or mixed with further components reactive with respect to isocyanate groups in 2K-PUR coating agents is described for example in EP-A 0 403 921, EP-A 0 639 628, EP-A 0 667 362, EP-A 0 689 881, U.S. Pat. No. 5,214,086, EP-A 0 699 696, EP-A 0 596 360, EP-A 0 893 458, DE-A 19 701 835 and U.S. Pat. No. 5,243,012.

The synthesis of polyaspartic acid esters is carried out by the addition of primary amines to an activated carbon double bond of vinylogous carbonyl compounds, as contained for example in maleic or fumaric acid esters and which is described in detail in the relevant literature (Houben Weyl, Meth. d. Org. Chemie Vol. 11/1, 272 (1957); Usp. Khim. 1969, 38,1933).

It has been found that this reaction sometimes does not go to completion during the synthesis (for example after 24 hours while stirring at 60° C.). The conversion rate of the reaction depends decisively on the type of primary polyamines used. The degree of conversion (measured on the basis of the concentrations of free, unreacted maleic and fumaric acid esters) after 1 day with 1,5-diamino-2-methylpentane is 90 to 93%. In contrast to this the degree of conversion when using a cycloaliphatic polyamine with sterically hindered amino groups (for example 4,4'-diamino-3,3'-dimethyldicyclohexylmethane) is only 77%. A complete or almost complete conversion is sometimes achieved only after several months.

These incompletely reacted products contain unreacted primary amino groups and possibly also free primary polyamines as well as the corresponding amount of unreacted maleic or fumaric acid esters. As a result, after the production of the products the latter continue to react during subsequent storage and accordingly the viscosity of the reaction mixture rises constantly until complete conversion has been attained. In addition, the reactivity of the product with respect to isocyanates decreases with the reduction in the concentration of primary amino groups. It is therefore sometimes not possible to ensure the establishment of a reproducible pot life.

Various solutions to the problem have already been described in the prior art, which however still do not provide ultimately satisfactory results.

It is possible to extend the reaction time or increase the reaction temperature. The first solution is often excluded for economic reasons. Increasing the reaction temperature to for example 80° C. or even 100° C. leads in turn to a increase in the color number of the product.

EP-A 0 667 362 and U.S. Pat. No. 5,243,012 describe extending the pot life of 2K-PUR binders based on polyisocyanates and polyaspartic acid esters by adding zeolites and/or organotin(IV) compounds. These measures are however only ameliorative and sometimes adversely affect other properties, and may for example lead to a turbidity of the lacquer or accelerate the NCO/OH reaction in the binder.

U.S. Pat. No. 5,821,326 describes how the reaction to produce monoaspartic acid and polyaspartic acid esters can be catalyzed by five-membered aromatic ring compounds. Although the catalysts used do indeed permit a more rapid conversion of the components, nevertheless in none of the quoted examples had a complete conversion of the reaction mixture been achieved within a reaction time of four days at 60° C. During the subsequent storage of the product mixture the viscosity of the product rises on account of the incomplete reaction.

In U.S. Pat. No. 5,216,170 the excess fumaric acid ester is removed by means of distillation and thus withdrawn from the reaction. This process is however time-consuming and energy-intensive and therefore does not provide a basis for a technically feasible process.

Accordingly, it is an object of the present invention to provide monoaspartic acid ester and polyaspartic acid ester systems that have an improved viscosity stability and thus storage stability without the quality of the resulting binders and/or coatings being adversely affected.

This object may be achieved by a thiol compound to an incompletely reacted reaction mixture, which during storage leads to a significantly lower rise in viscosity of the product and moreover the end product does not suffer from malodorous side effects due to the thiol compounds that are used. The effect of adding the thiol compound is that the unreacted portion of the vinylogous carbonyl compound is no longer available to undergo further reaction with the primary amines.

SUMMARY OF THE INVENTION

The present invention relates to a composition containing monoaspartic acid esters and polyaspartic acid esters of formula (I), $$X\text{---}[NH\text{---}CH(CH_2\text{---}COOR^2)\text{---}COOR^1]_m \quad (I)$$

in which
- X represents an m-valent organic radical obtained by removing the primary amino group or groups from a corresponding monoamine or polyamine in the molecular weight range from 60 to 6000 containing (cyclo)aliphatically or araliphatically bound primary amino groups,
- $R^1$ and $R^2$ represent identical or different organic radicals, and
- m represents an integer $\geq 1$, as well as an addition product prepared from a compound of formula (II) (component A), $$R^1OOC\text{---}CH\!=\!CH\text{---}COOR^2 \quad (II)$$

wherein the radicals $R^1$ and $R^2$ have the aforementioned meanings, and a thiol compound of the formula (III) (component B),

$$[HS]_n-R^3 \tag{III}$$

in which
R³ represents an n-valent organic radical optionally containing one or more heteroatoms, which may also contain other functional groups that are reactive or inert with respect to isocyanates, and
n represents an integer ≧1 and ≦4.

The compositions according to the invention are products having improved viscosity stability.

DETAILED DESCRIPTION OF THE INVENTION

The present invention also relates to a composition containing monoaspartic acid esters and polyaspartic acid esters of formula (I), $$X-[NH-CH(CH_2-COOR^2)-COOR^1]_m \tag{I}$$

in which
X represents an m-valent organic radical containing one or more heteroatoms, obtained by removing the primary amino group or groups from a corresponding monoamine or polyamine in the molecular weight range from 60 to 6000 containing (cyclo) aliphatically or araliphatically bound primary amino groups, which may contain further functional groups that are reactive with respect to isocyanate groups and/or are inert at temperatures up to
R¹ and R² represent identical or different alkyl radicals each having 1 to 18 carbon atoms and more particularly preferably represent identical or different alkyl radicals each having 1 to 8 carbon atoms, and
m represents an integer ≧2 and more preferably =2, as well as an addition product prepared from a compound of formula (II) (component A),

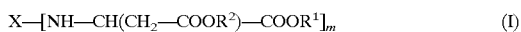
$$R^1OOC-CH=CH-COOR^2 \tag{II}$$

wherein the radical R¹ and R² have the aforementioned meanings,
and a thiol compound of the formula (III) (component B), $$[HS]_n-R^3 \tag{III}$$

in which
R³ represents an n-valent organic radical optionally containing one or more heteroatoms, which may also contain other functional groups that are reactive or inert with respect to isocyanates, and
n represents an integer ≧1 and ≦4.

The present invention also provides a process for the production of monoaspartic acid esters and polyaspartic acid esters of formula (I)

$$X-[NH-CH(CH_2-COOR^2)-COOR^1]_m \tag{I}$$

by reacting monoamines or polyamines of formula (IV) (component C),

$$X[-NH_2]_m \tag{IV}$$

with compounds of formula (II) (component A)

$$R^1OOC-CH=CH-COOR^2 \tag{II}$$

with a residual content of double bonds of 2 to 15% measured in terms of the double bonds present at the start of the reaction in the presence of at least one thiol compound of the formula (III) (component B),

$$[HS]_n-R^3 \tag{III},$$

in which
R³ represents an n-valent organic radical optionally containing one or more heteroatoms, which may also contain other functional groups that are reactive or inert with respect to isocyanates, and
n represents an integer ≧1 and ≦4.

The process according to the invention for the production of monoaspartic acid esters and/or polyaspartic acid esters of formula (I) is preferably carried out in two stages. In the first stage the components A and C are reacted at temperatures between 0° C. and 100° C., preferably 20° C. to 80° C. and more preferably 20° C. to 60° C., in a ratio of equivalents of primary amino groups of the component C to the C═C double bond equivalents of the component A of 1:1.2 to 1.2:1, preferably however 1:1.05 to 1.05:1, until the residual content of double bonds measured in terms of the double bonds present at the start of the reaction is 2 to 15%, preferably 5 to 10%. In the second stage unreacted double bond equivalents of the component A are reacted in the temperature range from 0° C. to 100° C., preferably 20° C. to 80 C. and more preferably 20° C. to 60° C., with the thiol groups of the component B in a molar ratio of 1.5:1 to 1:1, preferably 1.2:1 to 1:1, and more preferably 1.05:1.

A further suitable embodiment of the process according to the invention is the production of the monoaspartic acid and/or polyaspartic acid esters in three stages, wherein two different amines of the formula (IV) are used as component C1 and C2. In the first stage the components A and C1 are reacted at temperatures between 0° C. and 100° C., preferably 20° C. to 80° C. and particularly preferably 20° C. to 60° C., in a ratio of the equivalent of the primary amino groups of the component C1 to the C═C-double bond equivalents of the component A of 1:1.3 to 1:2, but preferably 1:1.5 to 1:1.7, until the residual content of primary amino groups is 0 to 15%, preferably 0 to 10%. The mixture is then reacted in the second stage with the component C2 in a temperature range from 0 C. to 100 C., preferably 20° C. to 80 C. and particularly preferably 20° C. to 60° C., so that the ratio of the sum of the equivalents of the amino groups of components C1 and C2 to the double bond equivalents of the component A is 1:1.2 to 1.2:1, preferably however 1:1.05 to 1.05:1. The reaction is carried out until 2 to 15%, preferably 5 to 10% of the double bonds still remain. In the third stage unreacted double bond equivalents of the component A are reacted with the thiol groups of the component B in a molar ratio of 1.5:1 to 1:1, preferably 1.2:1 to 1:1 and particularly preferably 1.05:1, in a temperature range from 0 C. to 10° C., preferably 20 C. to 80° C. and particularly preferably 20° C. to 60° C.

In the process according to the invention, in principle all known monoamines and polyamines having at least one primary amino group and that correspond to the formula (IV) may be used as component C.

Particularly suitable primary monoamines according to formula (IV) (m=1) include those monoamines that contain in their organic radical X one or more further functional groups that are either reactive or inert with respect to isocyanate groups. Examples include aminofunctional silanes such as for example 3-aminopropyltrimethoxysilane, 3-aminopropyltriethoxysilane or also aminoalcohols such as for example ethanolamine, propanolamine or isopropanolamine.

Preferred components C include polyamines of the formula (IV) where m represents an integer greater than or equal to 2. Examples include ethylenediamine, 1,2-diaminopropane, 1,4-diaminobutane, 2,5-diamino-2,5-dimethylhexane, 1,5-diamino-2-methylpentane (Dytek A, DuPont), 1,6-diaminohexane, 2,2,4- and/or 2,4,4-trimethyl-1,6-diaminohexane, 1,11-diaminoundecane, 1,12-diaminododecane or triaminononane.

Also suitable are higher molecular polyether polyamines with aliphatically bound primary amino groups such as are marketed by the company Huntsman, for example under the trade name Jeffamin. Polyamines of the formula (IV) in which m=2 and X represents a cyclic hydrocarbon radical with at least one cyclic carbon ring are more preferred in the process according to the invention. Examples of diamines that may particularly preferably be used include 1-amino-3,3,5-trimethyl-5-aminomethyl-cyclohexane (IPDA), 2,4- and/or 2,6-hexahydrotoluylenediamine ($H_6$TDA), isopropyl-2,4-diaminocyclohexane and/or isopropyl-2,6-diaminocyclohexane, 1,3-bis-(aminomethyl)cyclohexane, 2,4'- and/or 4,4'-diaminodicyclohexylmethane, 3,3'-dimethyl-4,4'-diaminodicylcohexylmethane (Laromin C 260, BASF AG), the isomeric diaminodicylcohexyl-methanes containing a methyl group as core substituent (=C-mono-methyidiaminodicyclohexylmethanes), 3(4)-aminomethyl-1-methylcyclohexylamine (AMCA) as well as araliphatic diamines, for example 1,3-bis-(aminomethyl) benzene.

Suitable components A include maleic or fumaric esters of formula (II) wherein $R^1$ and $R^2$ represent identical or different organic radicals each having 1 to 18 carbon atoms. Preferably $R^1$ and $R^2$ independently of one another represent linear or branched alkyl radicals with 1 to 8 carbon atoms.

Examples of component A include maleic acid dimethyl ester, diethyl ester, di-n-propyl or isopropyl ester, di-n-butyl ester, di-2-ethylhexyl ester or the corresponding fumaric acid esters.

Suitable components B include mercapto compounds of the general structural formula (III). Preferred mercapto compounds include trimethylolpropane-tri-(mercaptopropionate), pentaerythritol-tetra-(3-mercaptopropionate), glycol-di-(3-mercaptopropionate), glycol-dimercaptoacetate, trimethylolpropane-trithioglycolate, 2-ethylhexylthioglycolate, n-propylthioglycolate and/or isopropylthioglycolate, n-, iso- and/or tert.-butylthio-glycolate, mercapto diethyl ether, cyclohexylmercaptan, ethanedithiol, 1,4-butane-dithiol, 1,6-hexanedithiol, dodecanedithiol, didodecanedithiol, dimercaptobenzothiazole, allylmercaptan, benzylmercaptan, 2-mercaptoethanol, 2,3-dimercapto-propanol, α,α'-dimercapto-p-xylene, thiosalicylic acid, thiolactic acid, mercaptopropionic acid, mercaptoacetic acid, mercaptopyridine, dithioerythritol, 6-ethoxy-2-mercaptobenzothiazole, d-limonene-dimercaptan as well as liquid polysulfides such as are marketed by Marton Int. GmbH under the trade name LP, or mixtures thereof.

Particularly suitable examples of component B include esters of thioglycolic acid with linear or branched alcohols having at least 4 carbon atoms. Also suitable are thiols that contain further groups reactive with respect to isocyanates. Examples that may be mentioned here include 2,3-dimercapto-1-propanol, 2-mercaptoethanol, 3-mercapto-1,2-propanediol, ethylene glycol monothioglycolate, 2-hydroxyethyl-3-mercaptopropionate, 6-mercapto-1-hexanol, glycerol monothioglycolate, 4-mercaptobutanol, 11-mercapto-1-undecanol, cysteinol and glyceryl-3-mercapto-propionate. Also suitable are aliphatic monofunctional thiols having molecular weights of more than 146 g/mole, such as for example 1-octanethiol, dodecanethiol and didodecanethiol. Less preferred are mixtures of the aforementioned thiol compounds.

The production of the monoaspartic acid esters or polyaspartic acid esters of formula (I) according to the invention may be carried out in solution as well as in a solvent-free manner. The addition of solvents may however also take place only after the completion of the synthesis process, for example in order to reduce the viscosity. In principle all organic solvents are suitable as solvents, though of course it is preferred to use those solvents employed in coating technology. Examples include, though the list is not meant to be exhaustive, acetone, methyl ethyl ketone, methyl isobutyl ketone, n-butyl acetate, methoxypropyl acetate, toluene, xylene as well as higher aromatic solvents such as are marketed by Exxon-Chemie under the trade name Solvesso.

In a preferred embodiment of the invention the composition according to the invention contains
 a) 98 to 55 wt. % of a monoaspartic and polyaspartic acid ester of formula (I),
 b) 45 to 1 wt. % of an addition product prepared from a component A of formula (II) and a component B of the formula (III),
 c) 0 to 3 wt. % of free component A of formula (II),
 d) 0 to 1 wt. % of free component C of the formula (IV),
 with the proviso that the sum of a) to d) totals 100 wt. % based on a) to d),
 as well as optionally free component B of the formula (III) and optionally the conventional additives.

In a particularly preferred embodiment the composition according to the invention contains
 a) 97 to 71 wt. % of a monoaspartic and polyaspartic acid ester of formula (I),
 b) 29 to 3 wt. % of an addition product prepared from a component A of formula (II) and a component B of the formula (III),
 c) 0 to 0.5 wt. % of free component A of formula (II),
 d) 0 to 0.5 wt. % of free component C of the formula (IV),
 with the proviso that the sum of a) to d) totals 100 wt. % based on a) to d),
 as well as optionally free component B of the formula (III) and optionally the conventional additives.

The compositions according to the invention can be used directly after the completion of the synthesis process and, as regards reactivity, are stable over a period of several months and exhibit a significantly improved viscosity stability. On account of their low internal viscosity compared to the monoaspartic and polyaspartic acid esters that have been produced according to processes known in the prior art, the compositions according to the invention represent valuable reaction partners for polyisocyanates in low-solvent or solvent-free two-component polyurethane lacquers and coatings.

The present invention also provides for the use of the compositions according to the invention as reactive component in two-component polyurethane systems or for the production of prepolymers.

The two-component (2K) polyurethane systems containing the compositions according to the invention may then be used as coating agents for the production of coatings.

The invention is further illustrated but is not intended to be limited by the following examples in which all parts and percentages are by weight unless otherwise specified.

EXAMPLES

All percentages refer to percentages by weight unless otherwise specified.

A) Analysis of the Polyaspartic Acid Esters

The degree of conversion were determined on the basis of the signals from the methylene protons of the fumaric acid ester (into which maleic acid ester rearranges under base catalysis) and of the aspartic acid ester by means of $^1$H-NMR spectroscopy (400 MHz). The sample was dissolved in $CDCl_3$ to record the spectrum.

The viscosities were determined in a viscosimeter from Physika (conical plate). The shear gradient was 40-sec$^{-1}$.

B) Preparation of the Polyaspartic Acid Esters

I) General Procedure for the Preparation of the Polyaspartic Acid Esters (Comparison Examples)

One mole (2 g equiv.) of the diamine (component C) is placed under a nitrogen atmosphere in a 1 l capacity four-neck flask equipped with stirrer, dropping funnel, reflux cooler and internal thermometer, and 2 moles of maleic acid diethyl ester (344.36 g, component A) were added while stirring so that the temperature in the reaction mixture reached 50° C. but did not significantly exceed this value. The reaction mixture was then stirred for a further 60 to 180 hours at 600C. During the whole reaction time a gentle stream of nitrogen was passed over the reaction mixture.

I.1) Example 1 (Comparison Example)

Procedure as in (I):

| | | |
|---|---|---|
| 210.4 g | 4,4'-diaminodicyclohexylmethane (PACM 20; 1 mole) | |
| 344.4 g | Maleic acid diethyl ester (2 moles) | |
| | Reaction temperature | 60° C. |
| | Reaction duration | 90 hours |
| | Conversion | 95% |
| | Viscosity [mPa s/23° C.] | 1070 |

Storage: 4 weeks

After storage for four weeks at 50° C. the product had a conversion of 97% and a viscosity of 1400 mPa s/23° C.

I.2) Example 2 (Comparison Example)

| | | |
|---|---|---|
| 238.4 g | 3,3'-dimethyl-4,4'-diaminodicyclohexylmethane (Laromin C 260, BASF; 1 mole) | |
| 344.4 g | Maleic acid diethyl ester (MSDEE; 2 moles) | |
| | Reaction temperature | 60° C. |
| | Reaction duration | 90 hours |
| | Conversion | 90% |
| | Viscosity [mPa s/23° C.] | 870 |

Storage: 3 weeks

After storage for three weeks at 50 C. the product had a conversion of 95% and a viscosity of 1630 mPa s/23° C.

II) General Procedure for Preparing the Polyaspartic Acid Esters Under the Addition of Thioglycol Compounds (Example According to the Invention)

The procedure was as described in I). After completion of the reaction the product was cooled to room temperature and the thiol compound was added to the remaining fumaric acid diethyl ester (90 mole %) in such a way that the temperature did not exceed 60° C. The mixture was stirred for a further 4 hours at room temperature and decanted.

II.1) Example 3 (Example According to the Invention)

In the Examples 3, 4, 5 and 6 according to the invention and described hereinafter, the thiol compound was added after a reaction time of 90 hours.

| | |
|---|---|
| 4,4'-diaminodicyclohexylmethane (PACM 20; 1 mole) | |
| Maleic acid diethyl ester (2 moles) | |
| 2-ethylhexyl thioglycolate | |
| Reaction temperature | 60° C. |
| Reaction duration | 94 hours |
| Conversion | 99% |
| Viscosity [mPa s/23° C.] | 1000 |

Storage:

3 months at room temperature: conversion=99%; viscosity: 1200 mPa s/23° C.

4 weeks at 50° C.: conversion=99%; viscosity: 1200 mPa s/23° C.

II.2) Example 4 (Example According to the Invention)

| | |
|---|---|
| 4,4'-diaminodicyclohexylmethane (PACM 20; 1 mole) | |
| Maleic acid diethyl ester (2 moles) | |
| 1-dodecanethiol | |
| Reaction temperature | 60° C. |
| Reaction duration | 94 hours |
| Conversion | 99% |
| Viscosity [mPa s/23° C.] | 1000 |

Storage:

3 months at room temperature: conversion=99%; viscosity: 1000 mPa s/23° C.

4 weeks at 50° C.: conversion =99%; viscosity: 1080 mPa s/23° C.

II.3) Example 5 (Example According to the Invention)

| | | |
|---|---|---|
| 238.4 g | 3,3'-dimethyl-4,4'-diaminodicyclohexylmethane (Laromin C 260; 1 mole) | |
| 344.4 g | Maleic acid diethyl ester (MSDEE; 2 moles) | |
| 73.4 g | 2-ethylhexyl thioglycolate | |
| | Reaction temperature | 60° C. |
| | Reaction duration | 94 hours |
| | Conversion | 98% |
| | Viscosity [mPa s/23° C.] | 900 |

Storage:

3 weeks at 50° C.: conversion=99%; viscosity: 1000 mPa s/23° C.

II.4) Example 6 (Example According to the Invention)

| | | | |
|---|---|---|---|
| 238.4 g | 3,3'-dimethyl-4,4'-diaminodicyclohexylmethane (Laromin C 260; 1 mole) | | |
| 344.4 g | Maleic acid diethyl ester (MSDEE; 2 moles) | | |
| 72.8 g | 1-dodecanethiol | | |
| | Reaction temperature | 60° C. | |
| | Reaction duration | 94 hours | |
| | Conversion | 98% | |
| | Viscosity [mPa s/23° C.] | 900 | |

Storage:

3 months at room temperature: conversion=99%; viscosity: 980 mPa s/23° C.

C) Gelling Times of Coating Compositions

In the following examples coatings were produced by combination of the polyaspartic acid esters described in Examples 1 to 5 and polyisocyanates. In order to produce the coatings and to determine the gelling times, the polyaspartic acid esters were reacted with a polyisocyanate produced from 1,6-hexamethylene diisocyanate (Desmodur N 3600 from Bayer AG; viscosity: 1200 mPa s/23° C., NCO content: 23.4%, equivalent weight: 180 g) in an NCO:NH ratio of 1.05:1. The gelling time was the interval between the mixing of the two components up to the time at which the mixture could no longer be stirred.

TABLE 1

Gelling Times of Coating Compositions

| Coatings | 7 | 8 | 9 | 10 | 11 | 12 | 13 | 14 | 15 | 16 |
|---|---|---|---|---|---|---|---|---|---|---|
| Polyaspartic acid esters from Example # | 1 fresh | 1 stored* | 2 fresh | 2 stored* | 3 fresh | 3 stored* | 4 fresh | 4 stored* | 5 fresh | 5 stored* |
| Amount [g] | 60.6 | 60.6 | 63.9 | 63.9 | 61.0 | 61.0 | 61.0 | 61.0 | 64.6 | 64.6 |
| Desmodur N 3600 [g] | 41.4 | 41.4 | 41.4 | 41.4 | 37.1 | 37.1 | 37.1 | 37.1 | 35.4 | 35.4 |
| Gelling time [min] | 55 | 70 | 400 | >>400 | 55 | 55 | 55 | 55 | 400 | 420 |

*The storage time in each case was 3 months at room temperature.

The higher product stability of the aspartic acid esters can be seen by comparing the gelling times of the mixture given in Table 1 for the production of the coatings 7, 8, 9 and 10 (comparison examples) with the gelling times of the mixtures used to produce the coatings 11–14, 15 and 16 (aspartic acid esters according to the invention).

D) Measurement of the Shore Hardness

The measurements were carried out according to DIN 53505.

| Coatings | 7 | 8 | 9 | 10 | 11 | 12 | 13 | 14 | 15 | 16 |
|---|---|---|---|---|---|---|---|---|---|---|
| Shore hardness | 80 | 81 | 60 | 65 | 80 | 80 | 80 | 81 | 61 | 63 |
| | Polyaspartic acid esters from comparison examples | | | | Polyaspartic acid esters from examples according to the invention | | | | | |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A composition comprising monoaspartic acid esters and polyaspartic acid esters of formula (I), $$X-[NH-CH(CH_2-COOR^2)-COOR^1]_m \quad (I)$$

in which

X represents an m-valent organic radical, optionally having one or more heteroatoms, obtained by removing the primary amino group or groups from a corresponding monoamine or polyamine in the molecular weight range from 60 to 6000 containing (cyclo)aliphatically or araliphatically bound primary amino groups, and which may contain further functional groups that are reactive with respect to isocyanate groups and/or are inert at temperatures up to 100° C., $R^1$ and $R^2$ represent identical or different organic radicals, and m represents an integer $\geq 1$, as well as an addition product prepared from a compound of formula (II) (component A), $$R^1OOC-CH=CH-COOR^2 \quad (II)$$

and a thiol compound of formula (III) (component B), $$[HS]_n-R^3 \quad (III)$$

in which $R^3$ represents an n-valent organic radical optionally having one or more heteroatoms, which optionally may also have other functional groups that are reactive or inert with respect to isocyanates, and n represents an integer $\geq 1$ and $\leq 4$.

2. The composition of claim 1, wherein $R^1$ and $R^2$ have 1 to 18 carbon atoms.

3. The composition of claim 1, wherein $R^1$ and $R^2$ have 1 to 8 carbon atoms.

4. The composition of claim 1, comprising:
 a) 98 to 55 wt. % of a monoaspartic and polyaspartic acid ester of formula (I),
 b) 45 to 1 wt. % of an addition product prepared from a component A of formula (II) and a component B of formula (III),
 c) 0 to 3 wt. % of unreacted component A of formula (II),
 d) 0 to 1 wt. % of unreacted component C of the formula (IV), $$X[-NH_2]_m \quad (IV)$$

wherein X and m have the aforementioned meanings, with the proviso that the sum of a) to d) totals 100 wt. % based on a) to d),
as well as optionally free component B of the formula (III) and optionally the conventional additives.

5. A process for the production of monoaspartic acid esters and polyaspartic acid esters of formula (I), $$X-[NH-CH(CH_2-COOR^2)-COOR^1]_m \quad (I)$$

in which

X represents an m-valent organic radical, optionally comprising one or more heteroatoms, obtained by removing the primary amino group or groups from a corresponding monoamine or polyamine in the molecular weight range from 60 to 6000 containing (cyclo)aliphatically or araliphatically bound primary amino groups, and which may comprise further functional groups that are reactive with respect to isocyanate groups and/or are inert at temperatures up to 100 C., $R^1$ and $R^2$ represent identical or different organic radicals, and m represents an integer $\geq 1$, comprising reacting at least on monoamine or polyamine of the formula (IV) (component C), $$X[-NH_2]_m \quad (IV)$$

with at least one compound of formula (II) (component A)

$$R^1OOC-CH=CH-COOR^2 \quad (II)$$

with a residual content of double bonds of 2 to 15% measured in terms of the double bonds present at the start of the reaction, and adding at least one thiol compound of the formula (III) (component B), $$[HS]_n-R^3 \quad (III),$$

in which $R^3$ is an n-valent organic radical optionally having one or more heteroatoms, which optionally may also have other functional groups that are reactive or inert with respect to isocyanates, and n represents an integer $\geq 1$ and $\leq 4$.

6. The process of claim 5, wherein $R^1$ and $R^2$ represent identical or different alkyl radicals each having 1 to 18 carbon atoms.

7. The process of claim 5, wherein $R^1$ and $R^2$ represent identical or different alkyl radicals each having 1 to 8 carbon atoms.

8. The process of claim 5, wherein at least one thiol compound of the formula (III) (component B) has a residual content of double bonds of 5 to 10% measured in terms of the double bonds present at the start of the reaction.

9. The process of claim 5, wherein in a first stage the components A and C are reacted in a ratio of the equivalents of the primary amino groups of the component C to the C=C double bond equivalents of the component A of 1:1.2 to 1.2:1 and in a second stage unreacted double bond equivalents of the component A are reacted with the thiol groups of the component B in a molar ratio of 1.5:1 to 1:1.

10. The process of claim 5, wherein two different amines of the formula (IV) are used as component C1 and C2 and in a first stage the components A and C1 are reacted at temperatures between 0° C. and 100° C. in a ratio of the equivalent of the primary amino groups of the component C1 to the C=C-double bond equivalents of the component A of 1:1.3 to 1:2 until the residual content of primary amino groups is 0 to 15%, after which the mixture is then reacted in the second stage with the component C2 in a temperature range from 0 C. to 100 C., so that the ratio of the sum of the equivalents of the amino groups of components C1 and C2 to the double bond equivalents of the component A is 1:1.2 to 1.2:1 until 2 to 15% of the double bonds still remain after which in a third stage unreacted double bond equivalents of the component A are reacted with the thiol groups of the component B in a molar ratio of 1.5:1 to 1:1 in a temperature range from 0° C. to 100 C.

11. A prepolymer prepared by reacting a composition of claim 1.

12. A two-component polyurethane systems containing compositions according to claim 1.

* * * * *